(12) United States Patent
Fried

(10) Patent No.: US 9,895,251 B2
(45) Date of Patent: Feb. 20, 2018

(54) SPLINT AND METHOD OF USE

(71) Applicant: Scott Fried, Gwynedd Valley, PA (US)

(72) Inventor: Scott Fried, Gwynedd Valley, PA (US)

(*) Notice: Subject to any disclaimer, the term of this patent is extended or adjusted under 35 U.S.C. 154(b) by 404 days.

(21) Appl. No.: 14/663,626

(22) Filed: Mar. 20, 2015

(65) Prior Publication Data

US 2016/0270941 A1    Sep. 22, 2016

(51) Int. Cl.
*A61F 5/01* (2006.01)
*A61F 7/02* (2006.01)

(52) U.S. Cl.
CPC ...... *A61F 5/013* (2013.01); *A61F 2007/0233* (2013.01); *A61F 2007/0238* (2013.01)

(58) Field of Classification Search
CPC .... A61F 5/05866; A61F 5/013; A61F 5/0118; A61F 13/107; A61F 5/10; A61F 7/007; A61F 7/02; A61F 2013/00919; A61F 2007/0001; A61F 2013/00187; A41D 13/08; A41D 13/088; A63B 71/143
See application file for complete search history.

(56) References Cited

U.S. PATENT DOCUMENTS

| | | | | |
|---|---|---|---|---|
| 4,716,892 A | * | 1/1988 | Brunswick | A61F 5/0118 602/21 |
| 7,033,331 B1 | * | 4/2006 | Hely | A61F 5/0118 128/878 |
| 2005/0267391 A1 | * | 12/2005 | Garelick | A61F 5/0118 602/21 |

* cited by examiner

*Primary Examiner* — Ophelia A Hawthorne
(74) *Attorney, Agent, or Firm* — Garcia-Zamor IP Law; Ruy M. Garcia-Zamor

(57) ABSTRACT

A splint for facilitating the recovery of a person from injury, to provide additional support, or to prevent further injury from being done to one or more body parts, such as the arms, hands, and fingers. The splint may provide customizable and changeable embodiments to better assist a person in healing and may provide additional support.

10 Claims, 12 Drawing Sheets

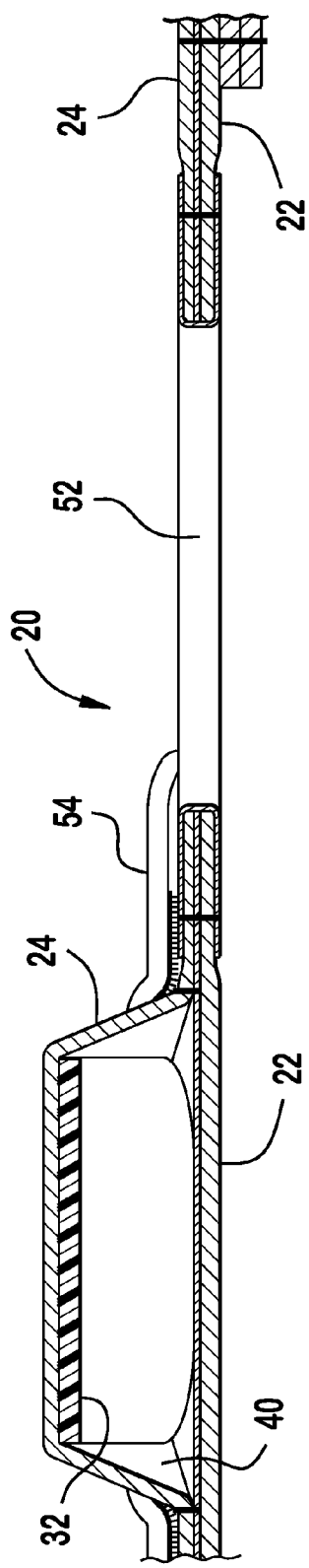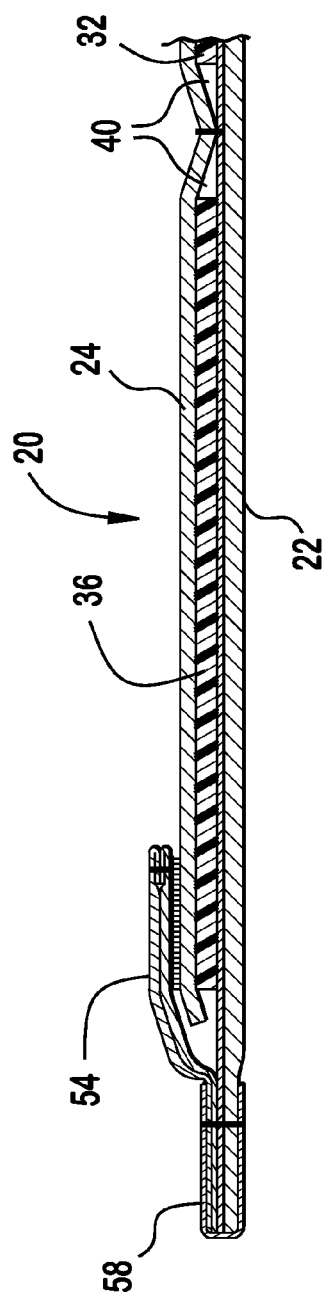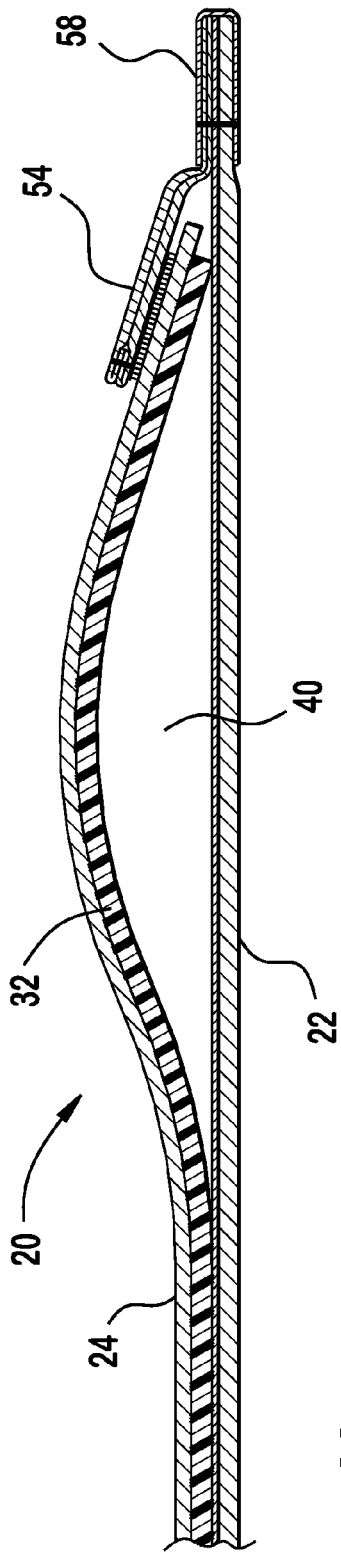

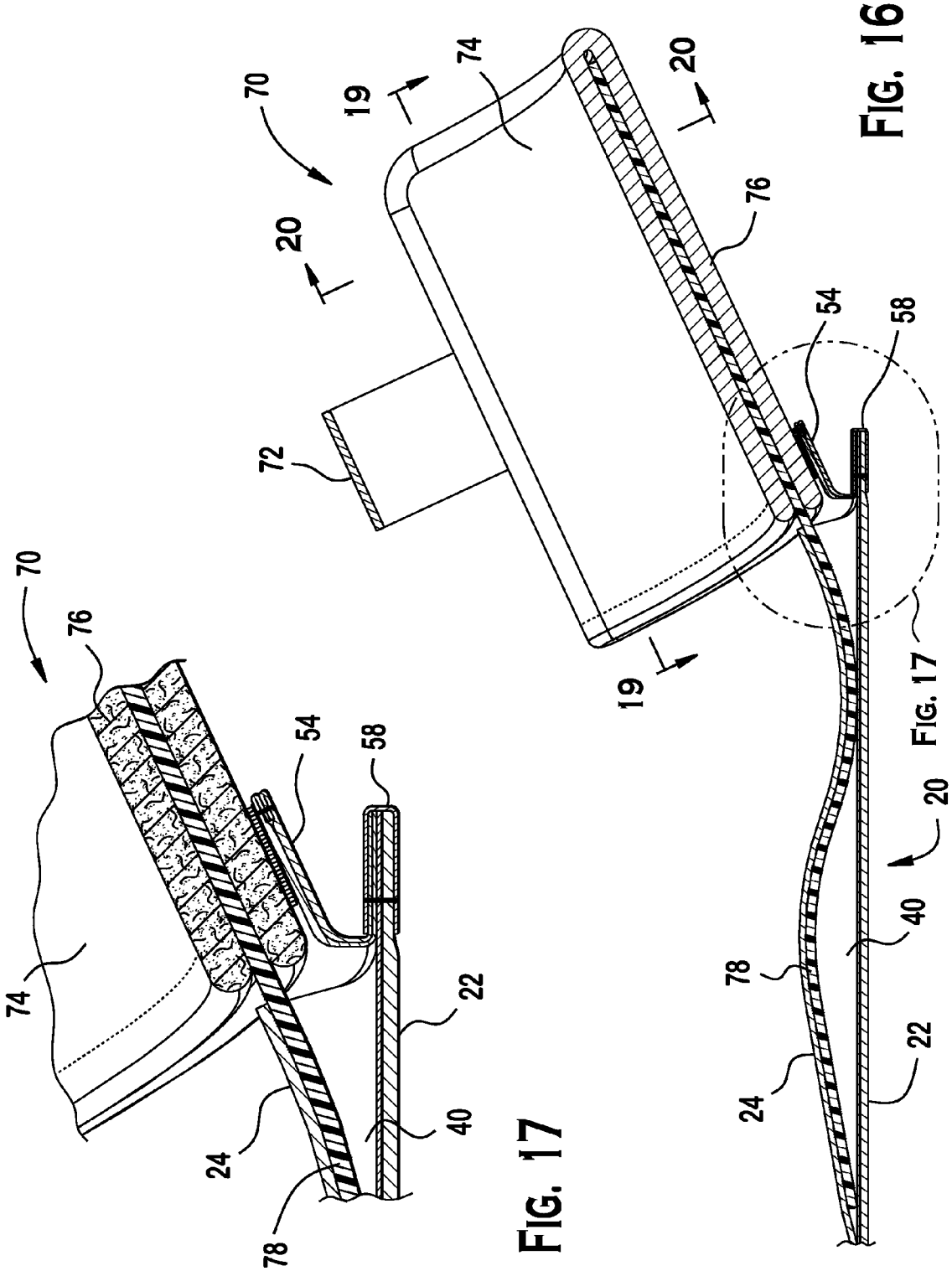

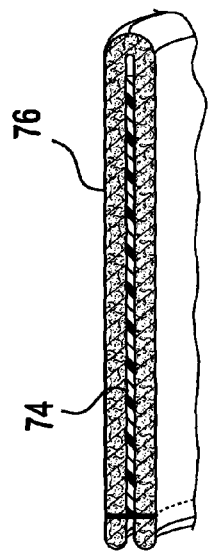
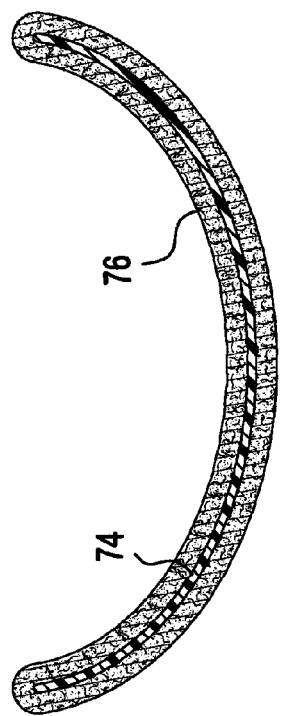
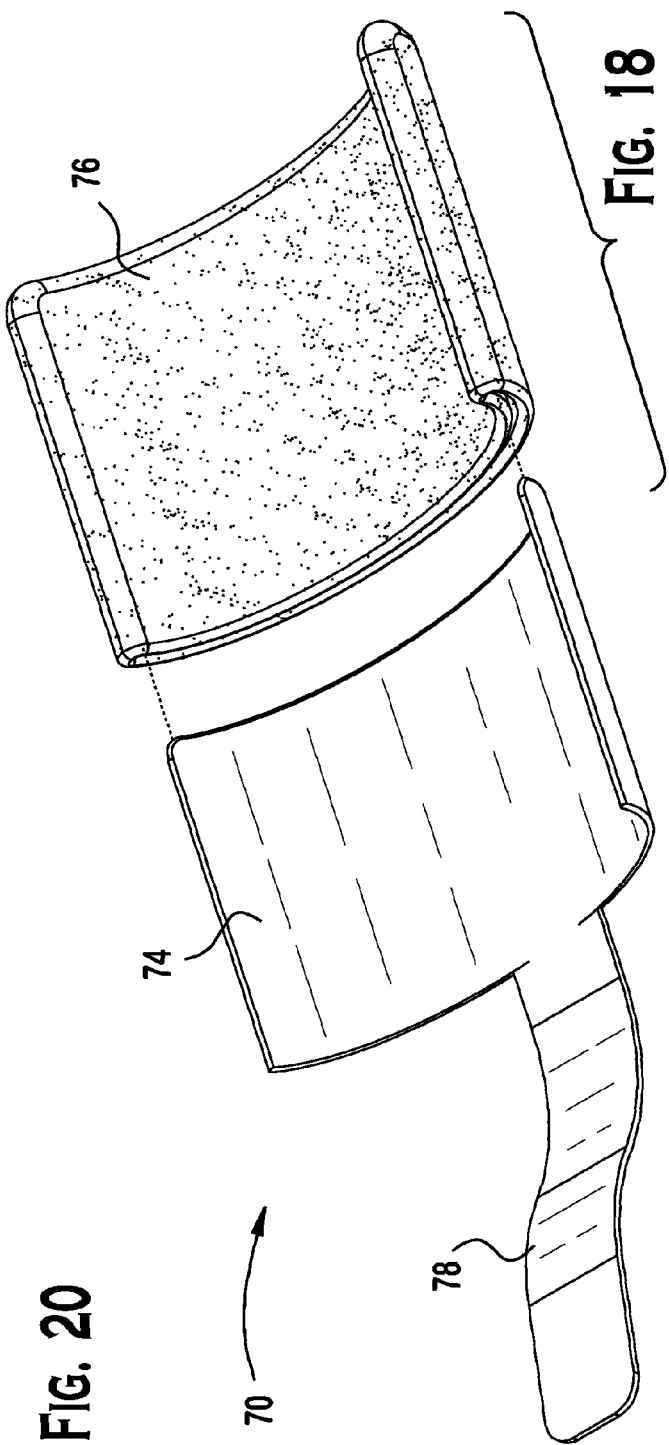
FIG. 19
FIG. 20
FIG. 18

SPLINT AND METHOD OF USE

BACKGROUND

The present invention relates generally to devices used for the support and immobilization of limbs and, more specifically, to a splint for a portion of the arm, wrist, and hand of a person.

Splints are commonly used to immobilize and support a limb. In many cases, the splint may immobilize a broken bone or damaged joint, or provide support for a joint during physical activity. A splint traditionally provides a prefabricated bandage member configured to enclose and often encase a limb, or portion of limb, in order to provide the required support and immobilization required for effective treatment and healing of the limb.

It may be advantageous to provide a splint which is customizable to a user's specific shape and movements; may conform to a desired orientation or shape; may provide additional support outside the main body of the splint; may provide adjustable supports; may allow for quick and efficient use; can be easily manufactured; and/or is preferably efficient to manufacture.

SUMMARY

In one aspect, one preferred embodiment of the present invention is directed to a splint adapted for use on at least a portion of an arm of a person. The splint may comprise a main splint body configured to wrap around a portion of the arm such that the splint extends longitudinally over at least a portion of the forearm, over the wrist, and/or over the first portion of the hand of a person. The main body may further comprise a pocket located on a side of the main splint body. A support member may also be positioned into the pocket. The support member is preferably configured to provide a contoured configuration to the main splint body and to provide resistance against moving the arm in a manner to drive the main splint body out of the contoured configuration.

In another aspect, one embodiment of the present invention is directed to a splint adapted for use on at least a portion of an arm of a person. The splint may comprise a main splint body configured to wrap around a portion of the arm such that the splint extends longitudinally over at least a portion of the forearm, over the wrist, and/or over the first portion of the hand of a person. The main body may further comprise a pocket located on a side of the main splint body. A support member may also be positioned into the pocket. The support member is preferably configured to be heated such that after heating, the support member is placed on the person and can then be configured such that the customized contoured configuration is provided to the person.

In another aspect, one embodiment of the present invention is directed to a splint adapted for use on at least a portion of an arm of a person. The splint may comprise a main splint body configured to wrap around a portion of the arm such that the splint extends longitudinally over at least a portion of the forearm, over the wrist, and/or over the first portion of the hand of a person. The main body may further comprise a pocket located on a side of the main splint body. A support member may also be positioned into the pocket such that the support member is removeable from and insertable into the pocket.

In another aspect, one embodiment of the present invention is directed to a splint adapted for use on at least a portion of an arm of a person. The splint may comprise a support member which is formed by an elongated member that is generally aligned parallel to a longitudinal axis of the splint.

In another aspect, one embodiment of the present invention is directed to a splint adapted for use on at least a portion of an arm of a person. The splint may further comprise a second support member which is configured for insertion into the main splint body. The second support member may be configured to provide a contoured configuration to the main splint body and to provide resistance against moving the arm in a manner to drive the main splint body out of the contoured configuration.

In another aspect, one embodiment of the present invention is directed to a splint adapted for use on at least a portion of an arm of a person. The splint may provide the ability to exchange the second support member with the support member. In this way, the support member may be removed from the pocket and the second support member may be disposed within the pocket.

In another aspect, one embodiment of the present invention is directed to a splint adapted for use on at least a portion of an arm of a person. The main splint body may further comprise a bore configured to receive a portion of the hand of the person in order to facilitate alignment of the main splint body on the arm.

In another aspect, one embodiment of the present invention is directed to a splint adapted for use on at least a portion of an arm of a person. The main splint body may further comprises a plurality of supplemental pockets and supplemental support members. The supplemental support members may be configured to be insertable and removeable from the plurality of supplemental pockets.

In another aspect, one embodiment of the present invention is directed to a splint adapted for use on at least a portion of an arm of a person. The plurality of supplemental pockets and plurality of supplemental support members may further be longitudinally aligned with the pocket such that one of the plurality of support members can be longitudinally aligned with either the support member or the second support member when they are disposed within the main splint body.

In another aspect, one embodiment of the present invention is directed toward a method of providing a splint adapted for use on at least a portion of an arm of a person. The method may further comprise providing a main splint body configured to wrap around a portion of the arm such that the splint extends longitudinally over at least a portion of a forearm, over a wrist, and/or over a first portion of a hand. The main body may further comprise a pocket. The method may also include providing a support member positioned in the pocket, the support member being configured to provide a contoured configuration to the main splint body and to provide resistance against moving the arm in a manner to drive the main splint body out of the contoured configuration.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 9 is a cross-sectional view of the main splint body of FIG. 5 as taken along the line 9-9 in FIG. 5. The figure illustrates the angled support member disposed within a pocket and enclosed by a corresponding tab.

FIG. 10 is a cross-sectional view of the main splint body of FIG. 5 as taken along the line 10-10 in FIG. 5. The figure illustrates the shortened support body disposed within a pocket of the main splint body.

FIG. 11 is a cross-sectional view of the main splint body of FIG. 5 as taken along the line 11-11 in FIG. 5. The figure illustrates a portion of the angled support member is position within a pocket of the main splint body and enclosed by a tab.

FIG. 16 is a partial side view cross section of the second support member of FIG. 12 disposed within a pocket of the main splint body. The arcuate extension is preferably angled away from the main splint body after insertion. A sleeve is preferably provided to enclose the arcuate extension of the second support body. The sleeve may further support the adjustable band of the second support member.

FIG. 17 is an enlarged partial view of the cross section of FIG. 16. When the second support member is disposed within the pocket of the main splint body, a tab is oriented in the open position to allow the arcuate extension to extend outwards.

FIG. 18 is a perspective view of the second support member. Preferably, the sleeve is provided as a separate member from the arcuate extension and configured to slide onto the arcuate extension. The sleeve may be disposable or interchangeable depending on surface comfort. Additionally, ice packs or heating gel can be incorporated into the sleeve without departing from the scope of the present invention. Alternatively, a fluid treatment can be incorporated into the sleeve, such as a moisturizer, burn cream, anti-biotic cream, etc. without departing from the scope of the present invention. While a preferred configuration of the arcuate extension is shown Those of ordinary skill in the art will appreciate from this disclosure that any desired shape of the arcuate extension can be used without departing from the scope of the present invention. Furthermore, the arcuate extension can have holes therethrough to reduce weight. While the arcuate extension is shown being integral with the second support member, Those of ordinary skill in the art will appreciate from this disclosure that the arcuate extension may be detachably engaged with the second support member. This can allow the arcuate extension to be added to the splint without having to interchange any support members in the main body of the splint.

FIG. 19 is a cross sectional view of the arcuate extension of FIG. 16 as taken along the line 19-19 of FIG. 16. The sleeve is preferably disposed on the arcuate extension.

FIG. 20 is a cross sectional view of the arcuate extension of FIG. 16 as taken along the line 20-20 of FIG. 16. The arcuate extension is provided with the sleeve in position thereover.

DETAILED DESCRIPTION OF THE PREFERRED EMBODIMENTS

Figure 1:
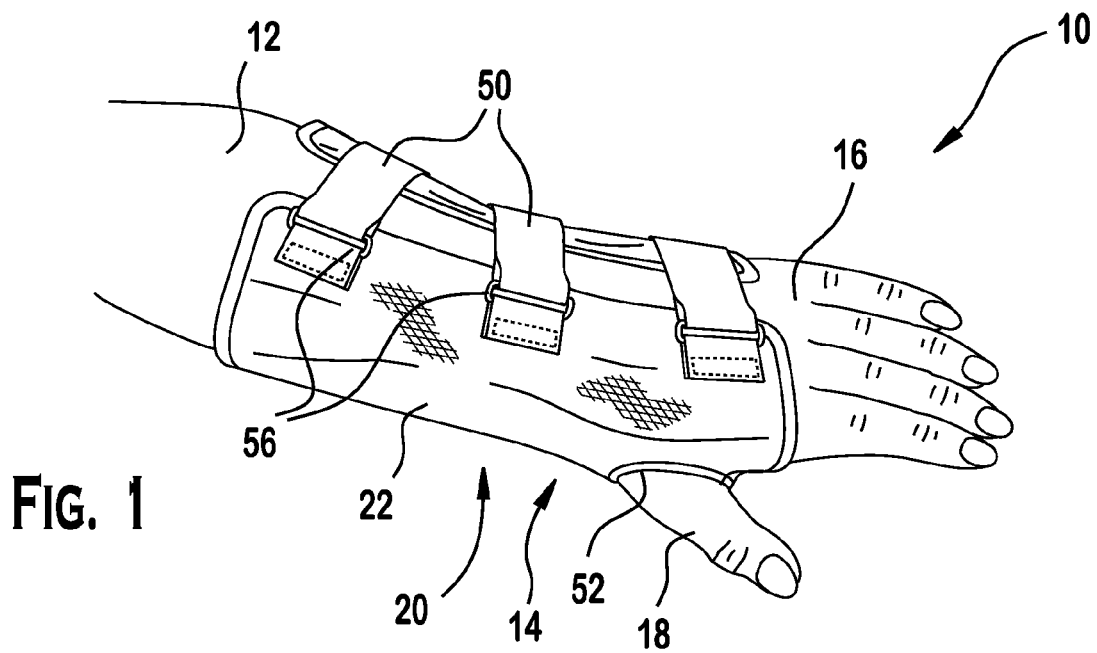
FIG. 1 is a perspective view of a preferred embodiment of the splint according to the present invention. The splint may be configured in place on a portion of person's forearm, wrist, and hand. Additionally, the splint is shown only partially enclosing the circumference of the arm, wrist, and forearm. Those of ordinary skill in the art will appreciate from this disclosure, however, that the splint may fully enclose the circumference of the arm during use, or only partially enclose the circumference without departing from the scope of the invention. Additionally, it shows that the splint may support a portion of the forearm, wrist, and hand, however, the splint may support any one of the above, or all of them, without departing from the scope of the invention.

Certain terminology is used in the following description for convenience only and is not limiting. The words "right", "left", "top", "bottom", designate directions in the drawings to which reference is made. The term "splint", as used in the claims and associated portions of the specification, is defined as meaning "any medical device used for the support and/or immobilization of limbs or appendages". "Vertical" refers to a generally up and down position, while "horizontal" refers to a generally left to right position. The term "longitudinal axis" is used throughout the claims and disclosure in reference to both the splint and the arm of a person. It should be understood that a longitudinal axis of the arm should generally refer to the length of the arm from the elbow to fingers as a general reference for positioning the splint. The term "interior", as used in the claims and corresponding portions of the specification means the side of the invention configured to contact the person. The term "exterior" similarly defines the surface generally oriented away from the person. The term "bore" refers to generally a through-hole within the main splint body. Additionally, the words "a" and "one" are defined as including one or more of the referenced items unless specifically stated otherwise. The terminology includes the words above specifically mentioned, derivatives thereof, and words of similar import.

Referring to FIGS. 1-20, wherein like numerals indicate like elements throughout, preferred embodiments of a splint according to the present invention are shown and generally designated as 10. Briefly speaking the splint 10 can be worn around an arm, a wrist, hand, and/or other limb of a person who is looking to provide additional support and/or immobilization to support health and recovery. The splint may fully or partially enclose the circumference of the arm, wrist, and/or hand without departing from the scope of the invention.

Referring now to FIG. 1, the splint 10 is preferably formed from a flexible, synthetic material such that the splint is configured to contour to the user's shape, however those of ordinary skill in the art will appreciate from this disclosure that any material, such as a cloth or bandage wrap may be used without departing from the scope of the invention. The splint is illustrated as enclosing the arm 12, wrist 14, and the hand 16 of a person, however, the splint may extend across any range of the person.

Figure 2:
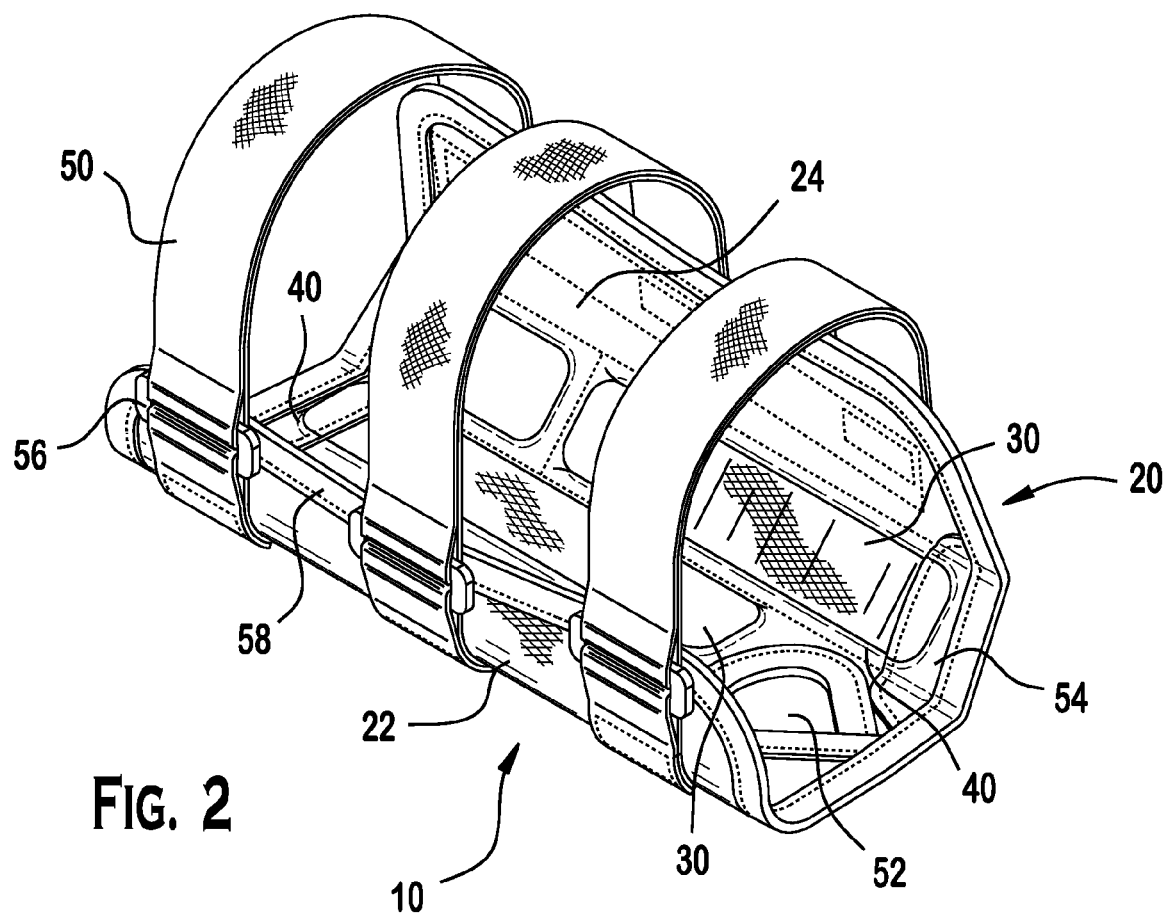
FIG. 2 is another perspective view of the splint of FIG. 1, without being placed in position on a person. The splint is preferably secured with three straps as illustrated, however, any number of straps may be used. Additionally, those of ordinary skill in the art will appreciate from this disclosure that any means of securement of the splint may be used without departing from the scope of the present invention. Several support members are illustrated in cut-away views disposed within pockets in the main body of the splint. The support members and pockets are preferably disposed longitudinally along the main splint body and aligned parallel with one another, however, those of ordinary skill in the art will appreciate from this disclosure that the support members may be configured in any orientation without departing from the scope of the present invention.

Referring to FIG. 2, a first preferred embodiment of the splint of the present invention is shown. The splint 10 may include a main body 20 which generally encloses the arm. The main body 20 can include a series of straps 50 which connect with buckles 56 to secure the main body onto the arm of the user. In a preferred embodiment, there are shown three straps 50, however, any number of straps or other securing means may be used to secure the splint 10. Additionally, the splint can be secured around a person's arm using snaps, hook and loop material, adhesive, etc. without departing from the scope of the present invention. The straps 50 are preferably attached on the exterior surface 22 of the main body 20. Pockets 40 are preferably disposed on the interior surface 24 of the main body 20. Support members 30 are additionally provided and configured to be removeable and insertable into the pockets 40. The support members 40 preferably have two major surfaces and when viewed from above have a generally rectilinear shape with rounded edges. Preferably, the shape of the pockets 40 corresponds to the support members 30, however, those of ordinary skill in the art will appreciate from this disclosure that a single pocket 40 may contain several support members 30 without departing from the scope of the present invention. The support members may have holes therethrough to lighten weight while still providing the necessary contouring and resistance to movement out of a contoured configuration to the sling.

Advantageously, the main body 20 may further comprise a bore 52 disposed as a through-hole between the exterior surface 22 and the interior surface 24 of the main body 20. The bore 52 is preferably tear-drop shaped, however, any shape may be used. A thumb 18 of the user is preferably positioned through the bore 50, such that the splint 10 individually encloses the hand 16 and a thumb 18 separately in order to provide a more customized and secure fit. As such, the bore 52 is preferably positioned on the main body 20 in such a location as to line-up with the thumb 18 when the splint 10 is in position, however, those of ordinary skill in the art will appreciate from this disclosure that the bore may be positioned anywhere along the main body 20 or omitted altogether without departing from the scope of the present invention. The interior surface 24 of the main body 20 is oriented such that is contacts the skin of the user and similarly wraps around the contours of the arm 12, wrist 14, and hand 16.

Figure 3:
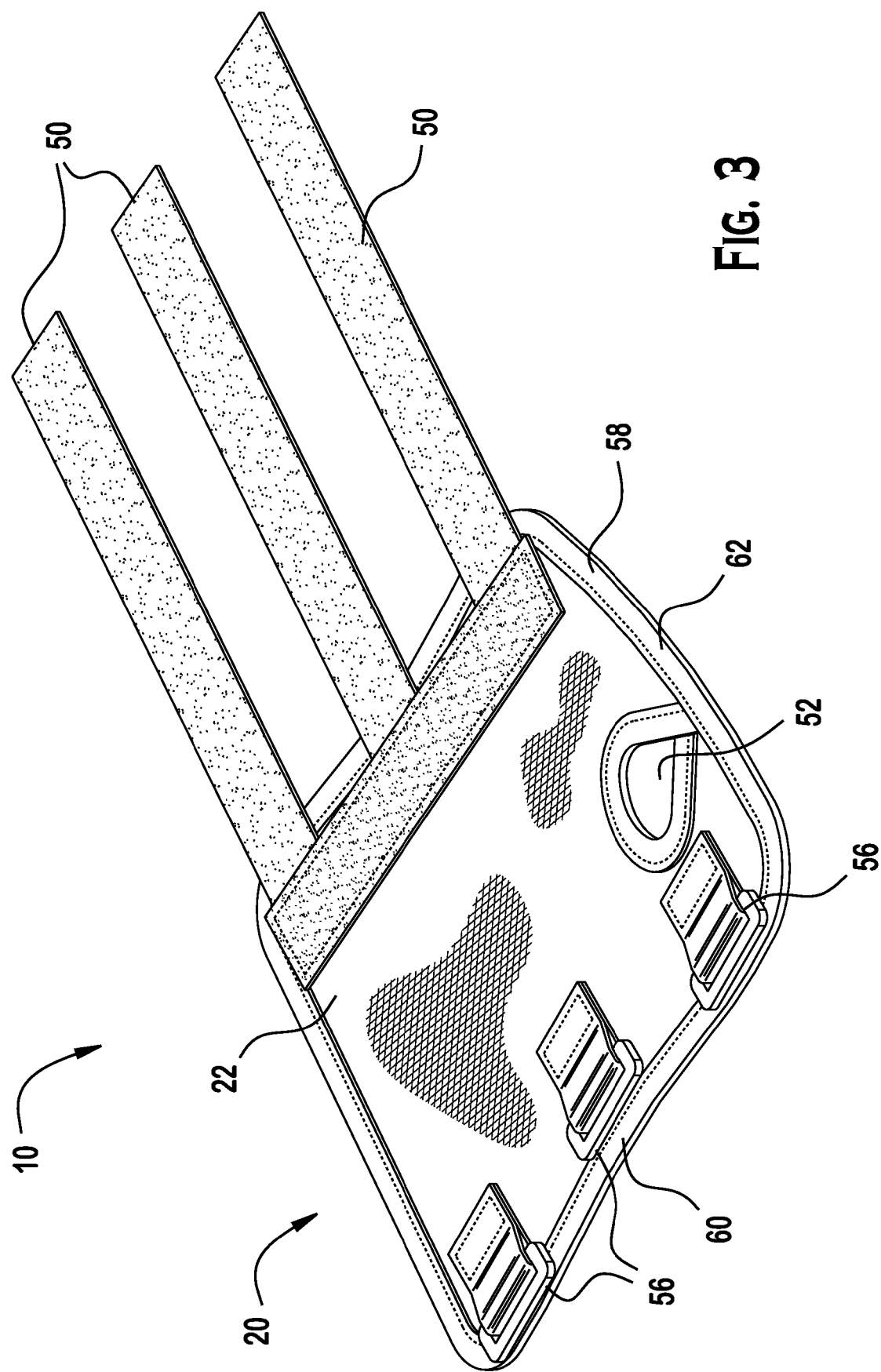
FIG. 3 is another perspective view of the exterior of main splint body of FIG. 1. The main splint body preferably attaches the straps to a lateral side of the exterior of the main splint body. A series of buckles are preferably attached on an opposing lateral side, such that when the splint is positioned in place, the straps may wrap around the users arm and wrist in order to secure to the opposing buckles. The strap and buckles may be disposed along any portion of the main splint body without departing from the scope of the present invention. Additionally, a bore is configured in the main splint body to preferably secure the thumb of the user, however, those of ordinary skill in the art will appreciate from this disclosure that the bore may be completely removed from the present invention or positioned for use with another finger without departing from the scope of the present invention.

Referring now to FIG. 3, an exterior surface 22 of the main body 20 of the splint 10 is shown. The exterior surface 22 preferably provides the attachment portions of the straps 50 and buckles 56. As illustrated, there are preferably three straps 50 and three corresponding buckles 56 positioned on opposing ends of the main body 20, however, any number of straps and buckles may be used. The bore 52 is illustrated as a through-hole in the main body 10, preferably positioned along a convex portion 62 of the main body 10 so as to facilitate insertion of the thumb 18 therethrough. The main body preferably has opposing lateral concave portions 60 and opposing lateral convex portions 62. In this way, the main body 20 preferably forms a generally rectilinear shape, however, those of ordinary skill in the art will appreciate form this disclosure that any shape may be used without departing from the scope of the present invention.

Figure 4:
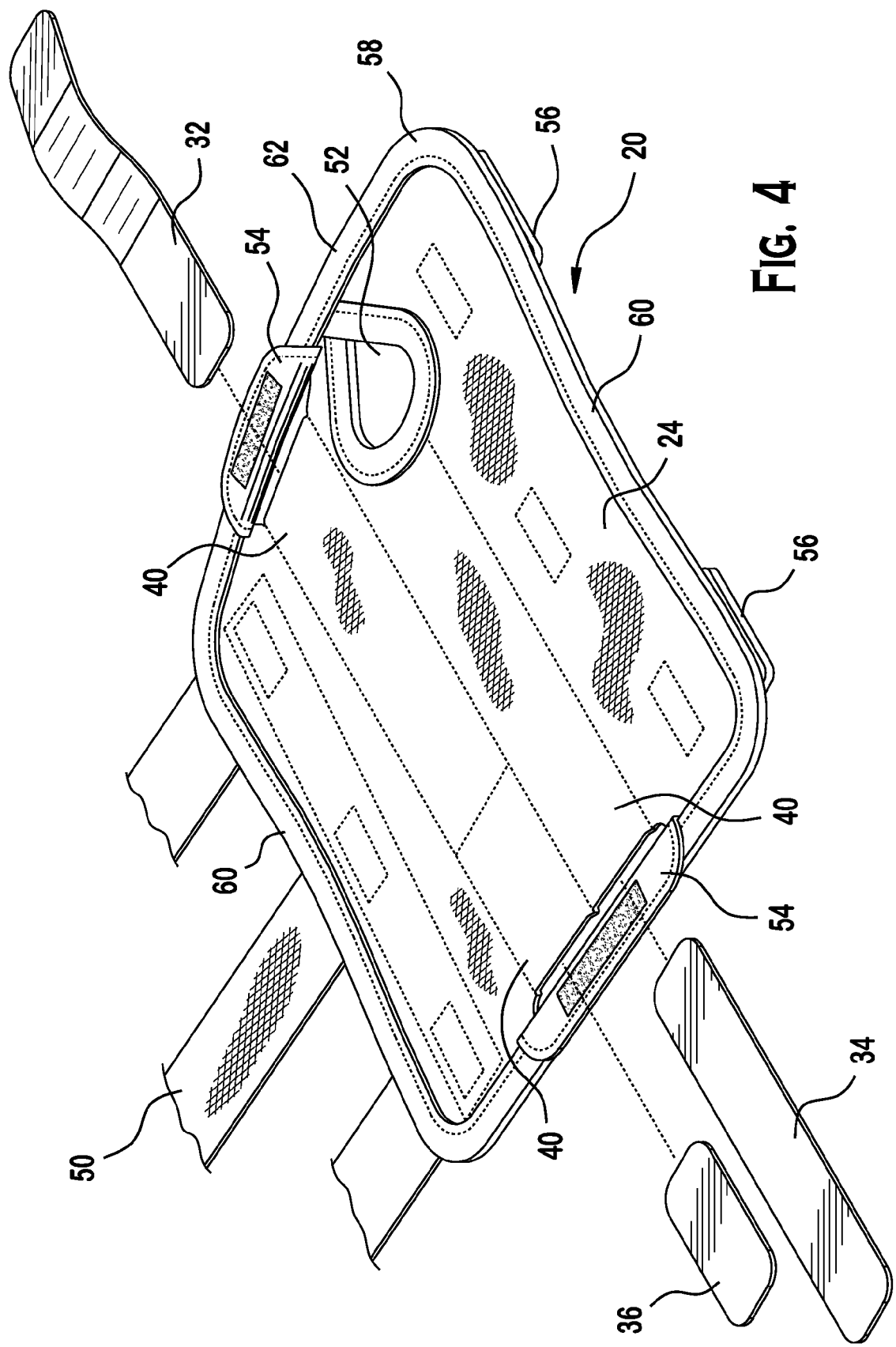
FIG. 4 is a perspective view of the interior of the main splint body of FIG. 1. Preferably, a number of support members are provided and configured to be insertable and removable from a plurality of pockets along the interior surface of the main splint body, however, those of ordinary skill in the art will appreciate from this disclosure that any number of support members and pockets may be used without departing from the scope of the present invention. Preferably, an angled support member, a flat support member, and a shortened support member are provided for insertion into pockets of corresponding size along the interior of the main splint body. Alternatively, the pockets may be disposed on the exterior of the main splint body without departing from the scope of the present invention.
Figure 5:
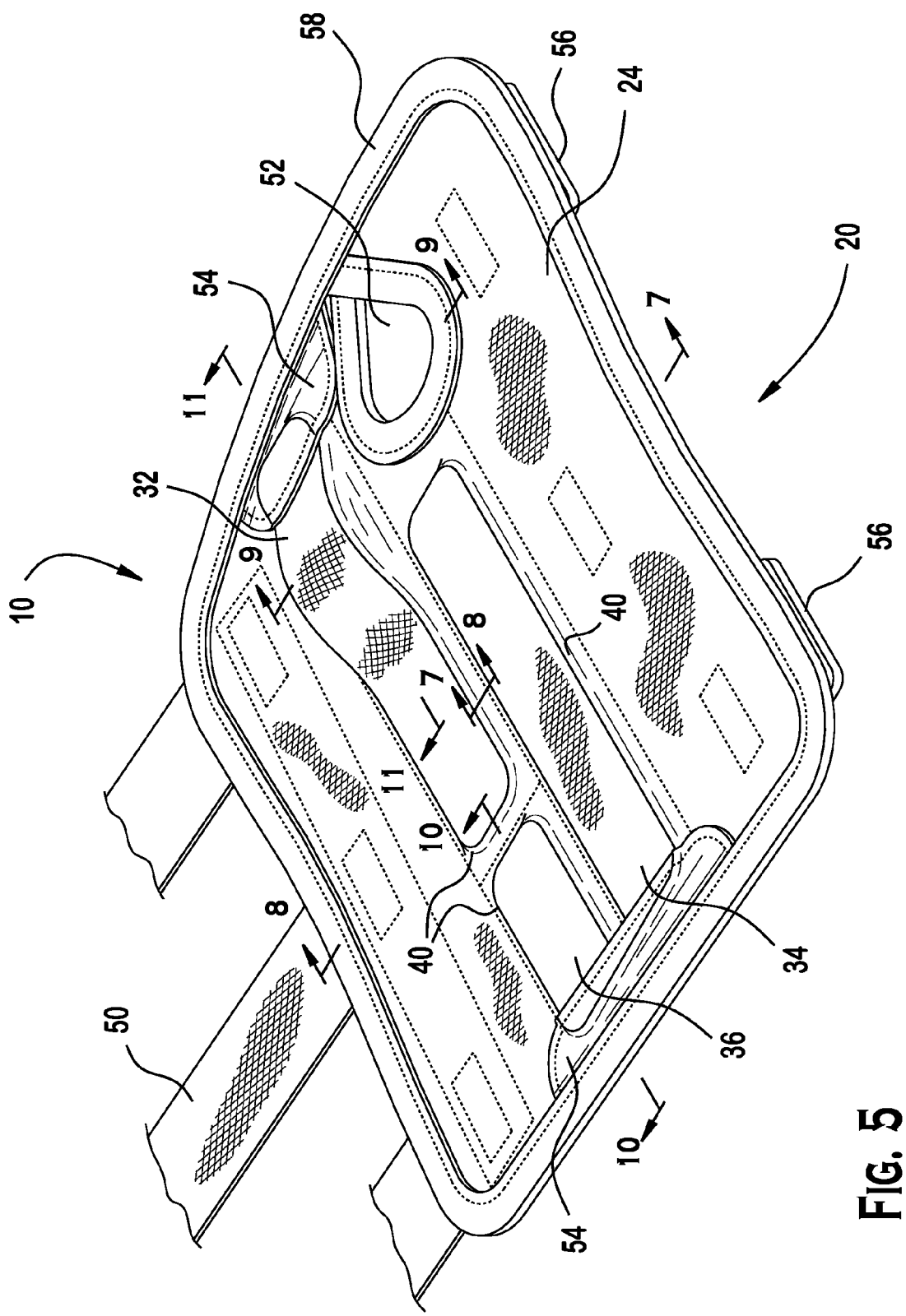
FIG. 5 is another perspective view of the interior of the main splint body of FIG. 1. The main splint body is shown with the support members in place within the pockets. While the support members are visible in the perspective view of the interior of the main splint body, in use, the support members are preferably concealed in the pockets of the main splint body. Preferably, the interior surface of the main splint body is configured of a flexible cloth material such that the material conforms to the contours of the support members, however, those of ordinary skill in the art will appreciate from this disclosure that any flexible material may be used without departing from the scope of the present invention. A series of tabs aligned with the pockets are provided to secure the support members within the pockets. A single tab me provided for multiple pockets or each pocket may be provided with an individual tab to secure the support members.
Figure 6:
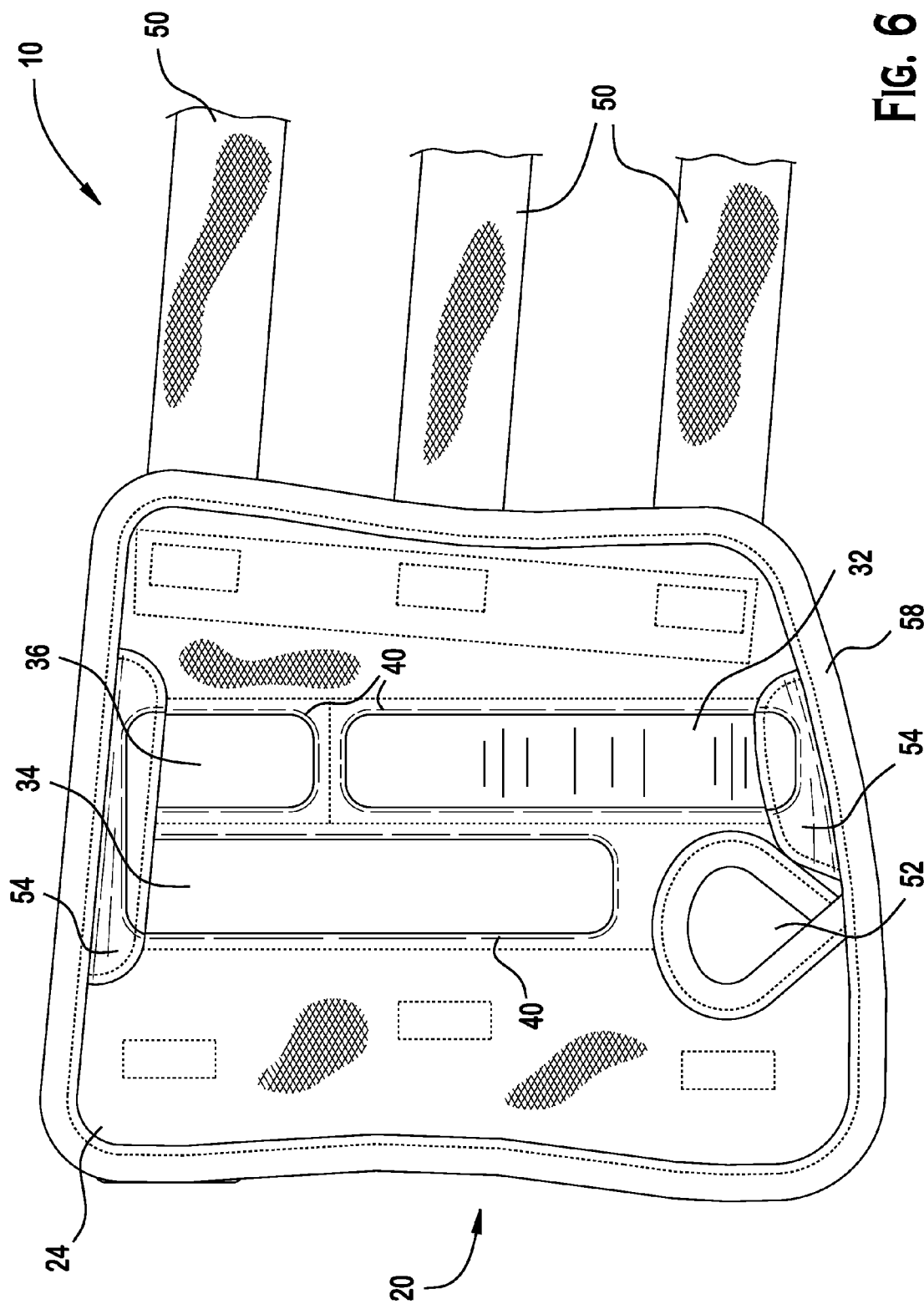
FIG. 6 is a top plan view of the interior of the main splint body of FIG. 1. A lining is preferably disposed about the perimeter of the main splint body as well as the bore provided for the thumb of the person. Those of ordinary skill in the art will appreciate from this disclosure that the lining may be completely removed from the present invention without departing from the scope of the present invention. As such, the entire main body can be formed of a single layer of material without departing from the scope of the present invention. A preferred embodiment of the present invention illustrates the flat and shortened support members enclosed with a single tab, while the angled support member is enclosed with a separate support member. Additionally, the support members are preferably inserted from opposing sides of the interior surface of the main splint body, however, those of ordinary skill in the art will appreciate from this disclosure that the support member may be inserted from any side of the main splint body without departing from the scope of the present invention. Alternatively, the support members may be attached to the main splint body with any suitable means of attachment, including hook and loop material, magnets, snaps, buttons, etc.
Figure 7:
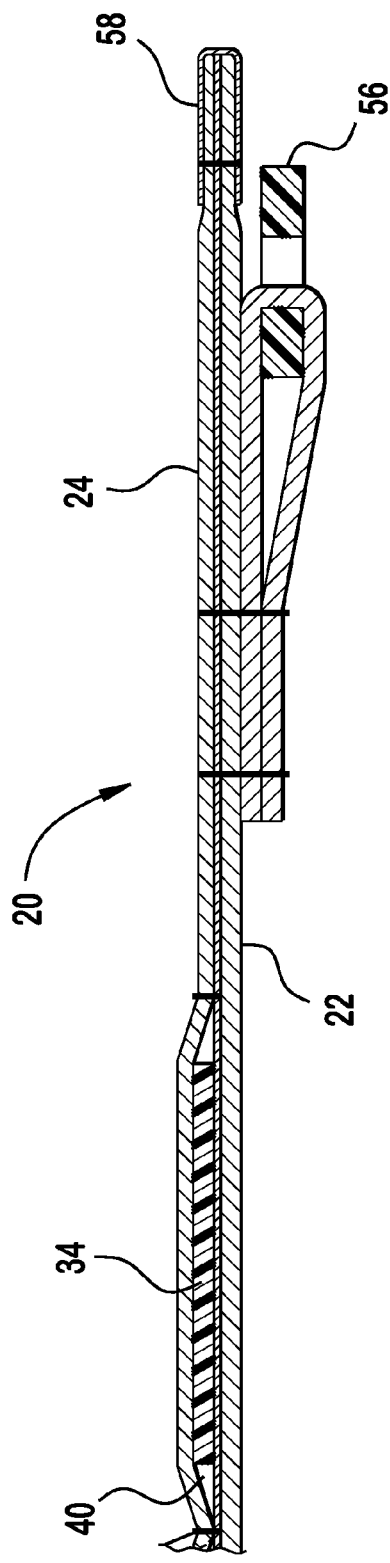
FIG. 7 is a cross-sectional view of the main splint body of FIG. 5 as taken along the line 7-7 in FIG. 5. The flat support member is shown inserted into a pocket in the main splint body. Additionally, a strap is shown disposed on the exterior of the main splint body.
Figure 8:
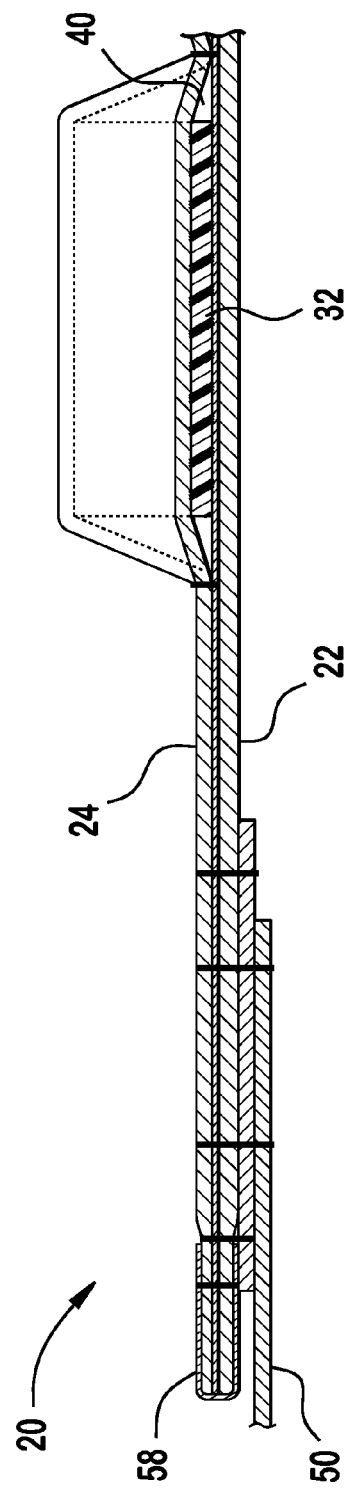
FIG. 8 is a cross-sectional view of the main splint body of FIG. 5 as taken along the line 8-8 in FIG. 5. A tab is illustrated in an open position to allow for insertion of a support member into a pocket. The main splint body is preferably provided with a strap on the exterior surface.
Figure 12:
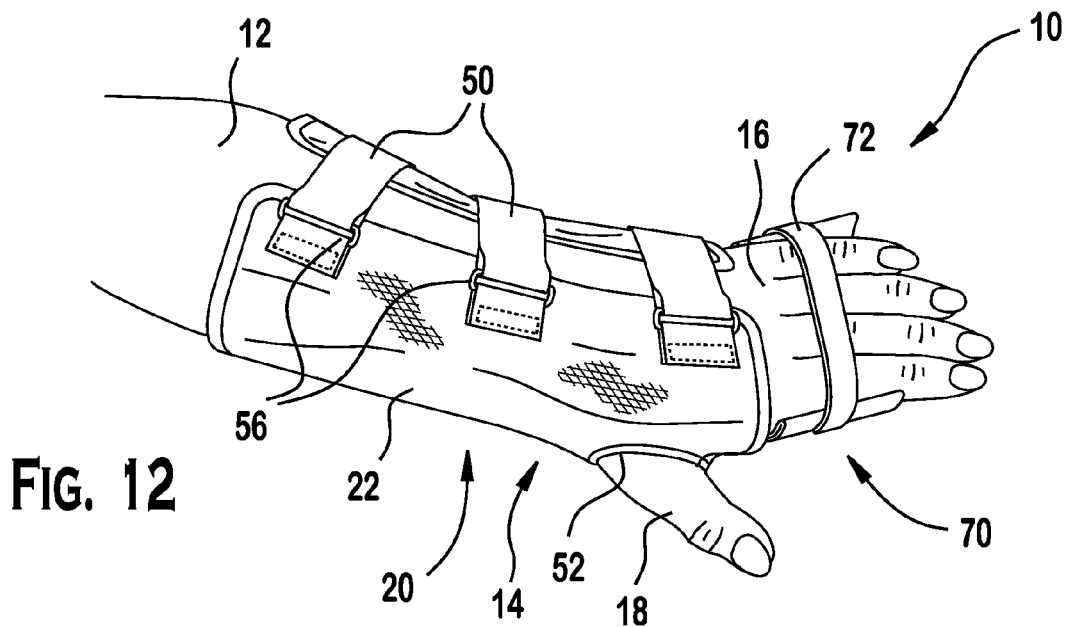
FIG. 12 is a perspective view of a second preferred embodiment of the splint of the present invention. A second support member is preferably provided to support and limit the movement of the fingers of the hand of the person. Those of ordinary skill in the art will appreciate from this disclosure that a second support member may provide support to any number of fingers or limbs without departing from the scope of the invention. The second support member is preferably disposed within a pocket of the main splint body and configured to extend outside of the pocket. The second support member may be configured to provide support to an individual finger or all fingers and may be used during sleep to provide additional support at night.
Figure 13:
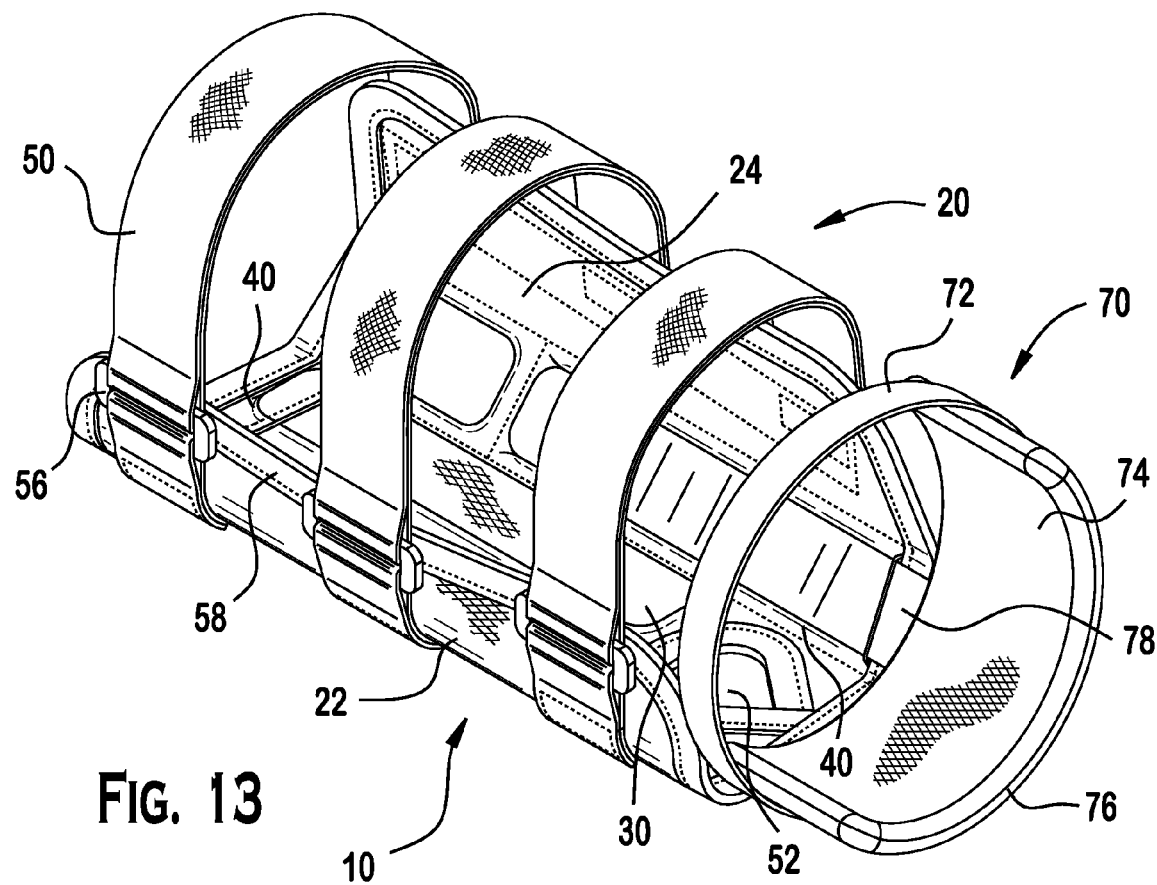
FIG. 13 is another perspective view of the main splint body of FIG. 12 with the second support member. The second support member preferably provides an arcuate extension on one end and an opposing end configured for insertion into the pocket of the main splint body. The arcuate extension 74 may alternatively be called a shield. Those of ordinary skill in the art will appreciate from this disclosure that the second support member may be provided with any shape or contour without departing from the scope of the present invention. Preferably, the second support member has an adjustable band configured to enclose the fingers and secure them in position within the second support member.

Referring now to FIGS. 4-6, an interior surface 24 of the main body 20 is illustrated. The interior surface 24 may further comprise pockets 40. The pockets 40 are configured so as to provide a free end along the convex portions 62 of the main body 20 configured to provide an opening. As such, support members 30 may be inserted into the pockets 40. The support members 30, as illustrated in FIG. 4, may include an angled support member 32, flat support member 34, and a shortened support member 36. The support members 30 are configured to provide a customized contour of the interior surface 24 of the main body 20 specific to the user of the splint. The support members may further be configured to be heat-formed such that upon heating, the support members may be adjusted and contoured to the specific shape of the arm 12, wrist 14, and hand 16 of the user. Preferably, the user may insert the support members 30 into pockets 40, heat the splint and support members, and then place the splint in position so that the support members form and cool to the shape of the user.

The support members 30 are preferably formed by an elongated member that generally aligned parallel to a longitudinal axis of the splint. The axis is generally aligned with a longitudinal axis of the arm 12 of the user. The pockets 40 preferably have a shape which generally corresponds to shape of the support members 30, however, those of ordinary skill in the art will appreciate from this disclosure that any size and shape pocket and support member may be used without departing from the scope of the present invention.

Referring more specifically to FIG. 5, the support members 30 may be inserted into the pockets 40 and are preferably fully enclosed therein. Tabs 54 may be provided along the lining 58 of the main body 20 to enclose the openings of the pockets 40 and to retain the support members 30 inside of the pockets.

Those of ordinary skill in the art will appreciate from this disclosure that the support members may be attached to the main body through any suitable attachment means, including VELCRO® brand hook-and-loop fastener, snaps, or buttons without departing from the scope of the present invention. Preferably, the angled support member 32 is disposed adjacent to a convex portion 62 of the main body and adjacent to the bore 52. The shortened support member 36 is preferably longitudinally aligned with the angled support member 32 along an opposing end of the main body 20. The flat support member 34 is preferably adjacent to the shortened support member 36, however, those of ordinary skill in the art will appreciate from this disclosure that the support members may be positioned anywhere along the main body without departing from the scope of the present invention.

Referring now to FIGS. 7-11, several section views of the splint according to FIG. 5 are shown. The interior surface 24 of the main body 20 preferably contours to the shape of the support members 30, whereas the outer surface of the main body can provide a smooth consistent contour around the circumference of the arm 12. It should be noted that the support members 30 may alternately be disposed along the exterior surface 22 of the main body without departing from the scope of the invention. Tabs 54 are further provides along the linin 58 of the interior surface 24 to enclose the openings of the pockets 40 once the support members are inserted into position. The tabs 54 may be of the same material as the main body 20 or of a separate rigid material. The tabs furthermore are preferably configured with a VELCRO® brand hook-and-loop fastener attachment to secure them to the interior surface 24, however, those of ordinary skill in the art will appreciate from this disclosure than any suitable attachment means may be used, such as a magnet, button, or zipper, without departing from the scope of the invention. With the support members 30 disposed within the pockets 40, the tabs 54 may be pressed onto the interior surface 24 against the support members to fully enclose them within the pockets. Referring specifically to FIG. 11, it should be noted that the interior surface 24 of the main body 20 contours to the shape of the angled support member 32, providing the customized contour configuration of the user's arm 12, wrist 14, and hand 16.

Figure 14:
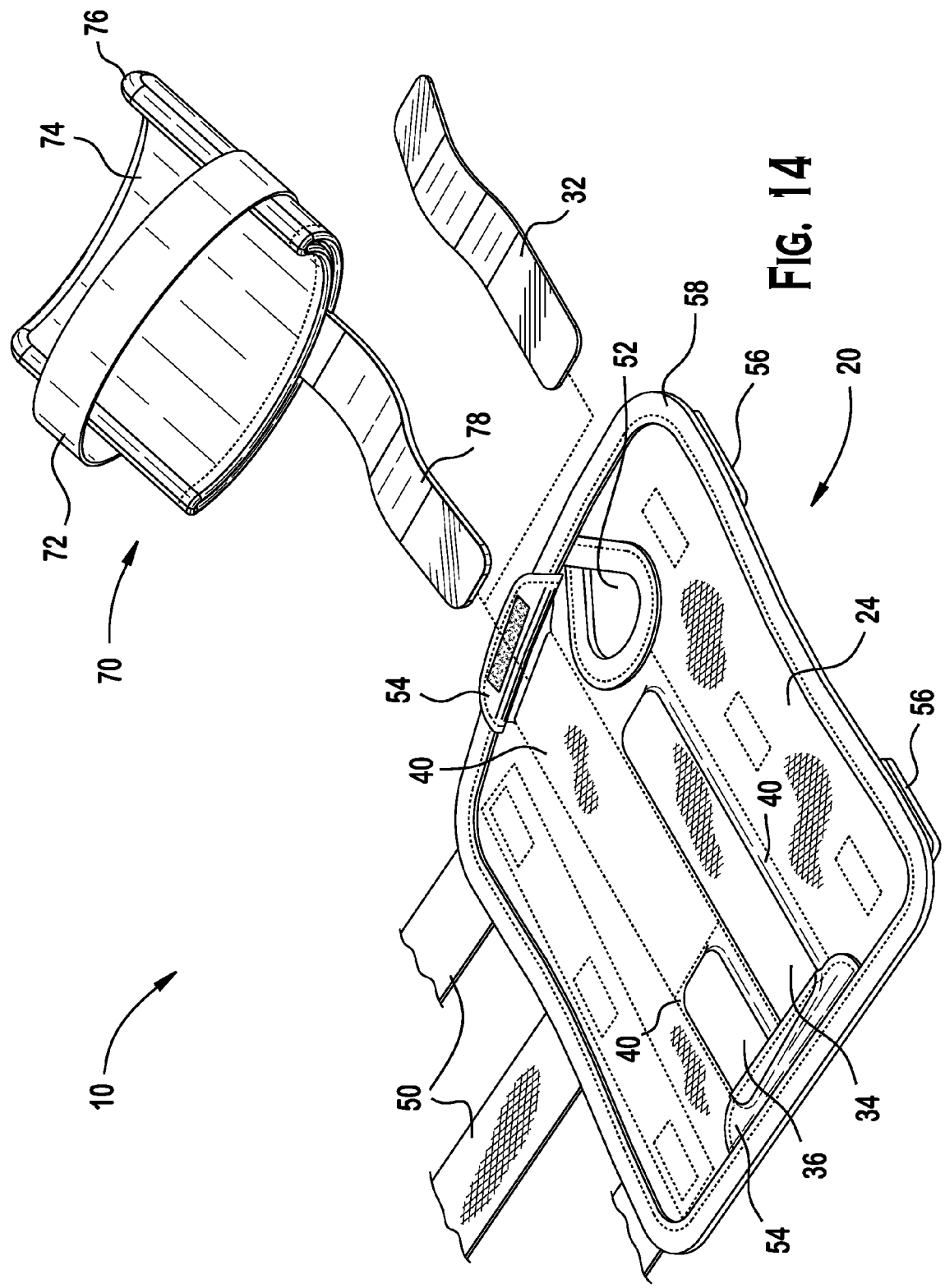
FIG. 14 is another perspective view of the main splint body of FIG. 12 with the second support member removed from the pocket. Preferably, the second support member is used in place of the angled support member, however, those of ordinary skill in the art will appreciate from this disclosure that any support member may be exchanged to use the second support member without departing from the scope of the present invention. Additionally, the second support member may be provided for use in addition to all the support members without the need for exchange.
Figure 15:
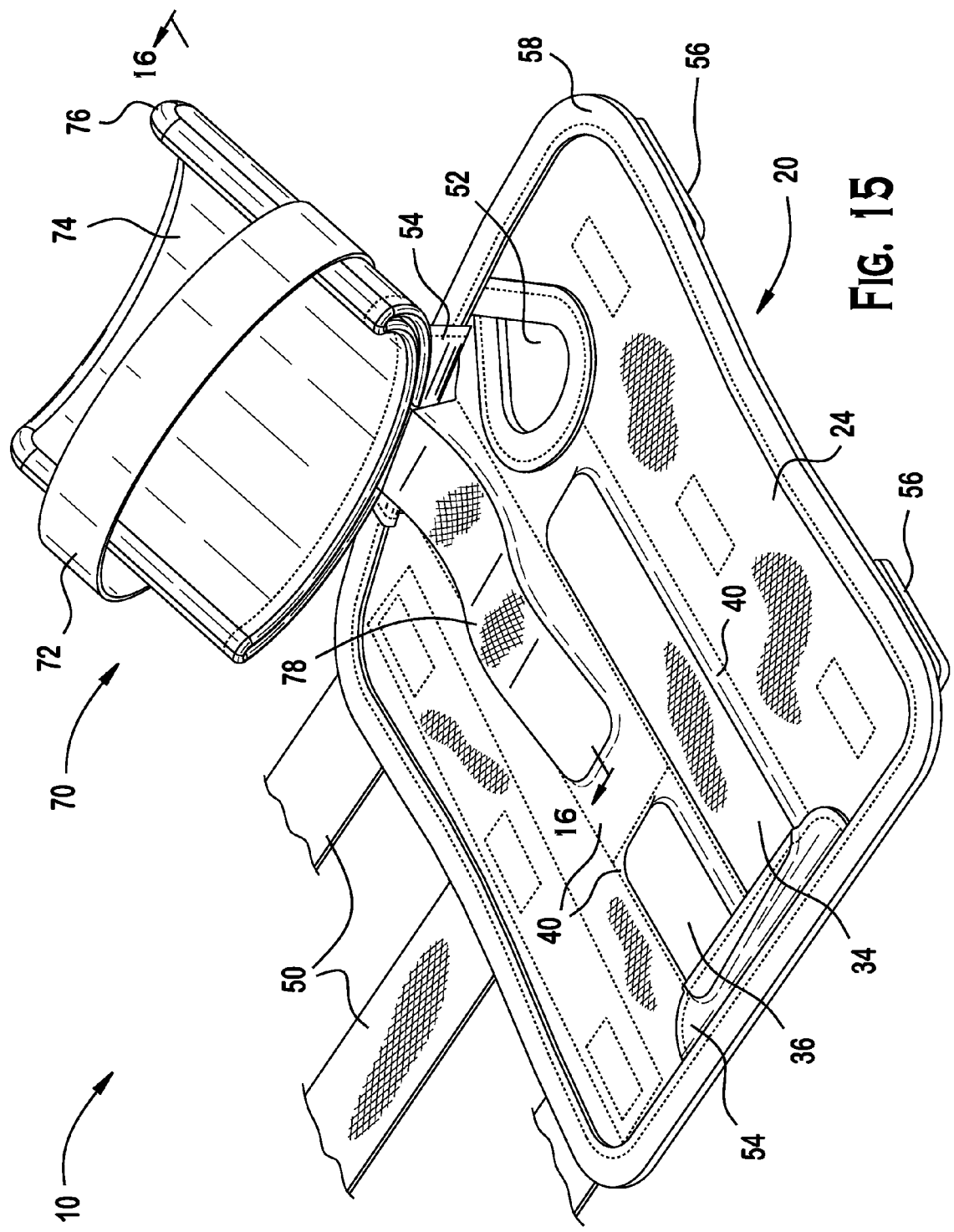
FIG. 15 is perspective view of the main splint body of FIG. 12 with the second support member inserted into a pocket of the main splint body. The second support member is preferably inserted into the pocket with the concave portion of the arcuate extension oriented toward the user's hand, however, the second support member may be oriented in any position without departing from the scope of the present invention.

Referring now to FIGS. 12-18, a second support member 70 may be provided as a separate attachment to the main body 20. The second support member 70 preferably provides an arcuate extension 74 and sleeve 76 which are configured to extend outside of the main body 20. The arcuate extension 74 may alternatively be called a shield. An adjustable band 72 may also be provided to secure the arcuate extension 74, or shield, to the hand 16 of the user. The adjustable band 72 is preferably attached to the sleeve 76 with VELCRO® brand hook-and-loop fastener, however, any suitable connections means, such as a button or clip may be used without departing from the scope of the present invention. A second support insert 78 may be further provided to insert into a pocket 40 to secure and position the second support member 70. The second support member may be configured to provide support and recovery from finger pain or "trigger finger" and is preferably used at night to provide support to the hand 16 during sleep. The second support member 70 is preferably exchangeable with the angled support member 32, however, those of ordinary skill in the art will appreciate from this disclosure that the second support member may be positioned anywhere and be exchanged or added to any support member of pocket of the splint without departing from the scope of the present invention. The second support member 70 preferably inserts into the pocket 40 until the arcuate extensions 74 comes into contact with the lining 58 of the main body 20. As such, the second support member 70 may be used in place of the angled support member 32, as illustrated in FIG. 14, depending upon the type and location of support desired by the user. The second support insert 78 preferably shares a similarly contoured shape as the angled support member 32, and also, is similarly dimensioned to fill the corresponding pocket 40, however, those of ordinary skill in the art will appreciate from this disclosure that the second support insert 78 may be of any shape or dimension and attach to the main body by any suitable means, as previously discussed in relation to the support members 30.

Referring more specifically to FIGS. 18-20, a preferred embodiment of the second support member 70 is shown. The second support member 70 preferably has a removeable sleeve 76 which is positioned over the arcuate extension 74. As illustrated, the second support member 70, including the arcuate extension 74 and the second support insert 78 are preferably made of the same material as the support members 30 and continuous throughout, however, those of ordinary skill in the art will appreciate from this disclosure that the second support member made be made of separate material or comprise separate parts without departing from the scope of the present invention. Similar to the support members 30, the second support member 70 is preferably heat-formable and customizable to the hand 16 of the user. Advantageously, the second support member 70 may therefore provide a customized fit and support to the user's hand 16 and fingers. The sleeve 76 is preferably a flexible material to follow the contours of the arcuate extension 74, and removeable to allow for cleaning and repositioning.

It should be noted that those of ordinary skill in the art will appreciate from this disclosure that the present invention may further be used in accordance with any medical device used for the support and/or immobilization of any limb (including the foot, leg, neck, etc.) without departing from the scope of the invention.

Referring to FIGS. 1-20, one preferred embodiment of the present invention operates as follows. A user places the appropriate support members 30 and/or second support member 70 in position within the pockets. The user then heats the splint 10 and support members 30, 70 to induce a suitable heat-forming temperature. Once the supports are heat-formable, the user may then place the splint around the arm 12, wrist 14, and hand 16, preferably with the thumb disposed through the bore 52, and secure the splint 10 with the straps 50. Once in place, the support members 30, 70 will contour to the shape of the user's features and solidify upon cooling, such that support and/or immobilization to the arm, wrist, and hand are provided in a customized and personalized splint.

It is recognized by those skilled in the art that changes may be made to the above described methods without departing from the broad inventive concept thereof. It is understood, therefore, that this invention is not limited to the particular embodiments disclosed, but is intended to cover all modifications which are within the spirit and scope of the invention as defined by the above specification, the appended claims and/or shown in the attached drawings.

What is claimed is:

1. A splint adapted for use on at least a portion of an arm of a person, the splint comprising:
    a main splint body configured to wrap around a portion of the arm such that the splint extends longitudinally over: at least a portion of a forearm, over a wrist, and over a first portion of a hand, the main body further comprising a pocket therein;
    a support member positioned in the pocket, the support member being configured to provide a contoured configuration to the main splint body and to provide resistance against moving the arm in a manner to drive the main splint body out of the contoured configuration;
    wherein the main splint body is configured such that the support member is removeable from and insertable into the pocket;
    wherein the support member is formed by an elongated member that is generally aligned parallel to a longitudinal axis of the splint; and
    wherein a second support member is configured for detachable insertion into the main splint body, the second support member being configured to provide the contoured configuration to the main splint body and to provide resistance against moving the arm in a manner to drive the main splint body out of the contoured configuration, the second support member being configured such that after insertion a portion of the second extension protrudes from the main splint body,
    a shield being positioned on the portion of the second support member such that when the second support member is fully inserted into the main splint body the shield is positioned adjacent to the main splint body, the shield being formed of rigid material, the shield being positioned generally adjacent to the main splint body to cover a portion of some of the fingers of the arm on which the main splint body is positioned when the second support member is inserted in the pocket, the shield being separate and spaced from the main splint body while being detachably connected thereto via the second support member.

2. The splint of claim 1, wherein the main splint body, with the support member located in the pocket, is configured to be heated such that after heating of the main splint body and placement of the main splint body on the person the main splint body can be configured such that the contoured configuration is customized to the person.

3. The splint of claim 2, wherein the pocket is sized in accordance with the support member such that the support member can be entirely disposed within the pocket.

4. The splint of claim 3, wherein the main splint body is configured such that the second support member is interchangeable with the support member such that the support member can be removed from the pocket and the second support member can be inserted into the pocket.

5. The splint of claim 4, wherein the second support member is configured to extend generally parallel to the longitudinal axis of the main splint body.

6. The splint of claim 5, wherein the main splint body is configured of a flexible material such that it generally conforms to the arm and to the contoured configuration.

7. The splint of claim 1, wherein the main splint body further comprises a bore configured to receive a portion of the hand to facilitate alignment of the main splint body on the arm.

8. A method of providing a splint adapted for use on at least a portion of an arm of a person, the method further comprising the steps of:

providing a main splint body configured to wrap around a portion of the arm such that the splint extends longitudinally over: at least a portion of a forearm, over a wrist, and over a first portion of a hand, the main body further comprising a pocket therein;

providing a support member positioned in the pocket, the support member being configured to provide a contoured configuration to the main splint body and to provide resistance against moving the arm in a manner to drive the main splint body out of the contoured configuration, the support member being removeable from and insertable into the pocket;

the main splint body, with the support member located in the pocket, being configured to be heated such that after heating of the main splint body and placement of the main splint body on the person, the main splint body can be configured such that the contoured configuration is customized to the person;

providing a second support member which is configured for detachable insertion into the main splint body, the second support member being configured to provide the contoured configuration to the main splint body and to provide resistance against moving the arm in a manner to drive the main splint body out of the contoured configuration, the second support member being configured such that after insertion a portion of the second extension protrudes from the main splint body;

providing a shield being positioned on the portion of the second support member such that when the second support member is fully inserted into the main splint body the shield is positioned adjacent to the main splint body, the shield being formed of rigid material, the shield being positioned generally adjacent to the main splint body to cover a portion of some of the fingers of the arm on which the main splint body is positioned when the second support member is inserted in the pocket, the shield being separate and spaced from the main splint body while being detachably connected thereto via the second support member.

9. The method of claim 8, wherein the step of providing the main step body further comprises a step of heating the main splint body and placing the main splint body on the person so that the main splint body can be configured such that the contoured configuration is customized to the person.

10. The method of claim 9, wherein the step of providing a second support member further comprises the main splint body being configured such that the second support member is interchangeable with the support member such that the support member can be removed from the pocket and the second support member can be inserted into the pocket.

* * * * *